United States Patent [19]

Drake

[11] Patent Number: 4,754,098

[45] Date of Patent: Jun. 28, 1988

[54] CATALYST COMPOSITIONS USEFUL FOR OLEFIN ISOMERIZATION AND DISPROPORTIONATION

[75] Inventor: Charles A. Drake, Nowata, Okla.

[73] Assignee: Phillips Petroleum Company, Bartlesville, Okla.

[21] Appl. No.: 31,829

[22] Filed: Mar. 30, 1987

Related U.S. Application Data

[62] Division of Ser. No. 832,547, Feb. 24, 1986, Pat. No. 4,684,760.

[51] Int. Cl.[4] .......... C07C 5/25; C07C 6/00

[52] U.S. Cl. .......... 585/646; 585/643; 585/647

[58] Field of Search .......... 585/643, 646, 647

[56] References Cited

U.S. PATENT DOCUMENTS

| | | | |
|---|---|---|---|
| 3,546,313 | 12/1970 | Banks | 585/643 |
| 3,660,506 | 5/1972 | Banks et al. | 585/643 |
| 3,767,565 | 10/1973 | Banks | 585/643 |
| 3,786,112 | 1/1974 | Reusser et al. | 585/643 |
| 4,287,378 | 9/1981 | Pennella | 585/643 |
| 4,490,477 | 12/1984 | Hobbs | 502/243 |
| 4,542,249 | 9/1985 | Reusser | 585/646 |
| 4,568,788 | 2/1986 | Kukes et al. | 585/646 |
| 4,605,810 | 8/1986 | Banks | 585/643 |
| 4,684,760 | 8/1987 | Drake | 585/670 |

*Primary Examiner*—Asok Pal

*Attorney, Agent, or Firm*—Williams, Phillips & Umphlett

[57] ABSTRACT

Catalyst composition is provided which is prepared by impregnating high surface area, high pore volume alumina with at least one magnesium compound convertible to the oxide, and, optionally, at least one alkali metal compound which is convertible to the oxide, and/or at least one zirconium compound convertible to the oxide, then subjecting the impregnated support to an oxygen-containing atmosphere under conditions suitable to convert at least a portion of the magnesium, alkali metal and zirconium compounds to the oxide form. The resulting catalyst is an effective double bond isomerization catalyst, and also greatly enhances the disproportionation activity of disproportionation catalysts when used in combination therewith.

7 Claims, No Drawings

CATALYST COMPOSITIONS USEFUL FOR OLEFIN ISOMERIZATION AND DISPROPORTIONATION

This is a division of application Ser. No. 832,547, filed Feb. 24, 1986, now allowed, U.S. Pat. No. 4,684,760.

This invention relates to the catalytic conversion of olefinic compounds. In one aspect, the invention relates to processes for the double bond isomerization of mono-olefins. In another aspect, the invention relates to catalysts for the double bond isomerization of mono-olefins. In yet another aspect, this invention relates to catalysts useful for the disproportionation of olefins. In a further aspect, this invention relates to process for the disproportionation of olefins.

BACKGROUND

Double bond isomerization, i.e., the shifting of the position of a double bond in an olefinic compound, is a well known phenomenon. Such an operation is frequently valuable in the conversion of one olefinic compound to one or more isomers thereof which may be less plentiful and more valuable. Olefinic compounds as a class are useful in themselves, such as for use as monomers to produce a wide variety of polymeric compositions, or for use as building blocks to prepare other still more valuable compounds.

A number of catalysts are known in the art to be active in double bond isomerization. However, such double bond isomerization is frequently accompanied by undesirable side reactions, such as for example, cracking, dehydrogenation, polymerization, and the like.

One use to which double bond isomerization catalysts have been put is as one component of a mixed disproportionation catalyst composition. The disproportionation, or metathesis, of olefins is a reaction in which one or more olefinic compounds are transformed into other olefins of different molecular weights. The addition of double bond isomerization catalysts thereto has been shown to increase the disproportionation activity of the disproportionation catalyst component.

By the term "disproportionation" or "metathesis" throughout this specification is meant the conversion of the feed olefinic (or unsaturated) hydrocarbon to a mixture of olefinic (or unsaturated) hydrocarbons having different numbers of carbon atoms than the feed hydrocarbons. The disproportionation of an olefin with itself to produce an olefin of a higher molecular weight and an olefin of a lower molecular weight can also be referred to as self-disproportionation. For example, propylene can be disproportionated to produce ethylene and cis-, and trans-2-butene. Another type of disproportionation involves the cross-disproportionation of two different olefins to form still other olefins. An example of the latter would be the reaction of one molecule of 2-butene with one molecule of 3-hexene to produce two molecules of 2-pentene.

While many catalyst compositions are known in the art for olefin disproportionation, it is a continuing objective of those of skill in the art to provide catalyst compositions having improved productivity, i.e., increased conversion of starting material and/or increased selectivity to the desired reaction product.

The present invention is based upon the discovery of novel double bond isomerization catalysts as well as the discovery of a way to dramatically improve the activity of disproportionation catalysts.

OBJECTS OF THE INVENTION

An object of the invention, therefore, is to provide catalysts useful for the double bond isomerization of olefinic compounds.

It is another object of the present invention to provide a process for the double bond isomerization of olefinic compounds whereby minimum by-product formation along with high selectivity to the double bond isomerized product is obtained.

Yet another object of the present invention is a catalyst composition and conversion process which give improved reactant selectivity and product yield upon the disproportionation of olefins.

These and other objects of the present invention will become apparent from the disclosure and claims herein provided.

STATEMENT OF THE INVENTION

In accordance with the present invention, I have discovered that highly active double bond isomerization catalysts are obtained when high surface area, high pore volume alumina is impregnated with at least one magnesium compound, and optionally at least one compound selected from the group consisting of alkali metal compounds and zirconium compounds, and thereafter subjecting the impregnated alumina support to an oxygen-containing atmosphere under conditions suitable to convert at least a portion of the magnesium, alkali metal, and zirconium compounds to the oxide form. Catalysts produced as described herein are highly active for the double bond isomerization of olefinic compounds, and are also useful components of mixed disproportionation catalyst systems wherein a disproportionation catalyst component and a double bond isomerization catalyst component are employed for olefin disproportionation.

DETAILED DESCRIPTION OF THE INVENTION

In accordance with the present invention, a method for preparing catalysts is provided which comprises impregnating an alumina support having a surface area of at least about 200 $m^2/g$ and a pore volume of at least 0.45 $cm^3/g$ with about 2 up to 20 weight % of at least one magnesium compound which is decomposable to the oxide, and, optionally, up to about 5 weight % each of at least one or both of an alkali metal compound which is decomposable to the oxide and a zirconium compound decomposable to the oxide, wherein each of the recited metal loadings are based on the weight of support is then subjected to an oxygen metal. The impregnated alumina support is then subjected to an oxygen containing atmosphere under conditions suitable to convert at least a portion of the magnesium, alkali metal, and zirconium compounds to the oxide form.

In accordance with another embodiment of the present invention, catalyst compositions prepared in accordance with the above described novel method are provided.

In accordance with yet another embodiment of the present invention, a process for the double bond isomerization of aliphatic olefinic hydrocarbon feeds is provided which comprises contacting the olefin feed under isomerization conditions with the catalyst composition prepared as described above.

In accordance with a further embodiment of the present invention, a disproportionation process is provided which comprises contacting at least one olefin under disproportionation conditions with a disproportionation catalyst system comprising a disproportionation catalyst and the double bond isomerization catalyst prepared as described herein above.

The alumina supports contemplated for use in accordance with the present invention have both high surface area and high pore volume. By "surface area" is meant alumina having a surface area of at least about 200 meters squared per gram ($m^2/g$), as measured by mercury surface area techniques.

By the term "high pore volume" is meant alumina having a pore volume of at least about 0.45 cubic centimeters per gram ($cm^3/g$), as measured by the mercury pore volume method. Preferred supports for use in the practice of the present invention are those having surface areas of at least about 220 $m^2/g$ and pore volumes of at least about 0.5 $cm^3/g$. Of course, those of skill in the art recognize that, in general, the higher the surface area, the lower the pore volume of a given support will be, and vice versa. Thus, catalyst supports having substantially higher surface areas than those specified herein will not be able to simultaneously achieve the desired high pore volumes; and conversely, catalyst supports having substantially higher pore volumes than those specified herein will not be able to simultaneously achieve the desired high surface areas. Therefore, the required minimum values set forth herein for surface area and pore volume indirectly place an upper limit as to how high these values may go.

In accordance with the present invention, the alumina support is impregnated with at least one magnesium compound which is decomposable to the oxide, and optionally with one or both of at least one alkali metal compound which is decomposable to the oxide, and at least one zirconium compound decomposable to the oxide. While those of skill in the art can readily determine suitable quantities of each compound to employ in the preparation of the invention catalysts, I have found that using quantities of each compound in the range set forth in Table I below provides active catalysts.

TABLE I

| | Metal Loadings, Wt. %* | | |
|---|---|---|---|
| | Broad | Preferred | Most Preferred |
| Mg compound | 1–20 | 2–10 | 6–9 |
| Alkali Metal compound | 0–5 | 0.2–5 | 0.4–2.5 |
| Zirconium compound | 0–5 | 0.3–3 | 0.5–2 |

*based on the weight of untreated alumina support and calculated as the elemental metal Suitable compounds which are convertible to the oxide form include the halides, oxides, sulfides, sulfates, nitrates, acetates, carbonates, oxylates, and the like, and mixtures of any two or more thereof.

Exemplary magnesium compounds include magnesium nitrate, magnesium carbonate, magnesium oxalate, magnesium hydroxide, magnesium chloride, and the like, as well as mixtures of any two or more thereof.

Exemplary alkali metal compounds, when optionally employed, include lithium nitrate, sodium nitrate, potassium nitrate, cesium nitrate, lithium carbonate, sodium carbonate, potassium carbonate, lithium oxalate, sodium oxalate, potassium oxalate, lithium hydroxide, sodium hydroxide, potassium hydroxide, lithium chloride, lithium iodide, lithium bromide, sodium chloride, sodium iodide, potassium chloride, potassium iodide, and the like, and mixtures of any two or more thereof.

Exemplary zirconium compounds, when optionally employed, include zirconium nitrate, zirconium hydroxide, zirconium chloride, and the like, as well as mixtures of any two or more thereof.

The alumina support and compounds to be impregnated thereon can be contacted in any suitable manner. For example, the alumina support and support-treating reagents can be mixed in an open vessel. When the support-treating reagents are provided as a solution, such as for example, an aqueous solution, once the alumina support and support-treating solution are mixed, then any excess liquid can be decanted or removed by filtration. Alternatively, the technique of incipient wetness can be employed whereby only enough liquid is employed to thoroughly wet the support, with no residual liquid. Thus, only as much support-treating solution is employed as the alumina support can absorb. This can be accomplished, for example, by spraying support-treating solution over a quantity of alumina which is being tumbled in a rotating, baffled drum. Such treatment can also be carried out by simply pouring a predetermined quanitity of support-treating solution over a quantity of alumina support contained in an open vessel. Alternatively, a measured quantity of alumina support could be added to a volume of support-treating solution such that all the liquid is imbided by the added support. Other techniques as are known to those skilled in the art can also be employed. For example, a quantity of alumina support may be placed in a tubular reactor, a volume of support-treating solution may be percolated therethrough, followed by further treatment/activation as necessary.

The conditions of alumina support/support-treating reagent contacting are not critical. Any temperature and any period of contact time is suitable. For convenience, contacting is generally carried out at about room temperature, although higher or lower temperatures can be employed. When support-treating reagents are provided as an aqueous solution, contacting is preferably carried out at a temperature not exceeding about 100° C. A time period sufficient to allow the support and reagents to come into intimate contact is all that is necessary. Thus, the alumina support and support-treating reagents may be brought into contact for as little time as a few seconds to several hours or more, as convenient.

Following contact of the alumina support and support-treating reagents, any excess liquid (if solvent or diluent is employed) can be removed by suitable means, such as, for example, decantation, filtration, or the like. The treated support can then be dried to remove absorbed solvent. Any suitable means, as well known by those skilled in the art, may be employed, such as for example, oven drying, passing a vigorous stream of dry (moisture-free) gas over the treated support, and the like. For example, the impregnated alumina support, prepared as described herein above, can be dried by heating at an elevated temperature of about 200° C. or higher by passage of an inert gas such as nitrogen over the impregnated support. This can be accomplished within the reactor or in other suitable catalyst preparation equipment.

Dried, impregnated support is then treated in the presence of an oxygen-containing gas, such as for example, air, under conditions sufficient to convert at least a portion of the magnesium and, if employed, the alkali metal and zirconium compounds, to the oxide form. Temperatures in the range of about 200° C. up to about 800° C. are generally satisfactory for such treatment. The time for subjecting the impregnated alumina support to the oxygen-containing gas is an amount of time sufficient to cause oxidation of at least a portion of the magnesium, alkali metal, and zirconium compounds to the oxide form. Anywhere from a few minutes to several hours is suitable. Typically, about 15 minutes up to about 20 hours of such treatment will be sufficient. Preferably, for most efficient use of reaction equipment, the dried, impregnated alumina support will be subjected to oxygen-containing atmosphere for about 30 minutes up to about 6 hours. Typically, less time is required at higher temperatures, and vice versa. The resulting catalyst composition comprises 1-20 weight % magnesium oxide, calculated as the metal and based on the weight of the support, impregnated on a high surface area, high pore volume alumina support, optionally containing up to 5 weight % of at least one alkali metal oxide and/or up to 5 weight % of zirconium oxide also impregnated thereon.

Aliphatic mono- and polyenes having more than three carbon atoms are amenable to isomerization or disproportionation treatment employing the catalyst of this invention, including cyclic compounds and branched chain as well as normal chain compounds. In general, olefins suitable for treatment in accordance with the present invention are aliphatic or alicyclic olefinic hydrocarbons having from 4 to about 30 carbon atoms, inclusive. Preferably, the practice of the isomerization embodiment of the present invention is carried out with a feed comprising mono-olefinic hydrocarbons.

Representative examples of mono-olefins useful in the practice of the isomerization embodiment of the present invention include butenes, pentenes, hexenes, octenes, decenes, and the like as well as mixtures of any two or more thereof.

In carrying out isomerization reactions with the catalyst of the invention, suitable reaction conditions or isomerization conditions can be used which effectively cause double bond isomerization of the olefins present in the feed. In general, the temperature at which isomerization is affected with this catalyst is about 150°-600° C. Preferably the temperature will be in the range of about 250°-500° C. Reaction pressure can vary appreciably and can be either super- or subatmospheric. Generally, reaction pressure will not exceed about 40 atmospheres in order to avoid condensation reactions that ultimately lead to excessive coke formation on the catalyst. Preferably, a reaction pressure in the range of atmospheric pressure up to about 1000 psig will be employed for the most favorable trade-off between rate of reaction, operating and equipment costs, etc.

The isomerization reaction of the present invention can be carried out in both the liquid and gaseous phase. When reaction is carried out in the gas phase, contact time of reactants on the catalyst can be expressed as gas hourly space velocity (GHSV) and can range between about 100 to 1000. Preferably, GHSV will range between about 200 and 750. When the isomerization reaction of the present invention is carried out in the liquid phase, contact time of reactants on the catalyst can be expressed as liquid hourly space velocity (LHSV) and can range between about 0.1 and 10. Preferably LHSV will range between about 0.5 and 10.

In accordance with a specific embodiment of the present invention, the double bond isomerization catalyst described herein above can be admixed with a disproportionation catalyst. The addition of the invention double bond isomerization catalyst to a disproportionation catalyst provides increased olefin feed conversion compared to disproportionation reactions employing disproportionation catalyst alone.

A wide variety of disproportionation catalysts can be used in the practice of this embodiment of the present invention. Preferred catalysts are those selected from the group consisting of:

tungsten oxide on silica,
molybdenum oxide on alumina,
molybdenum oxide on silica,
cobalt molybdate on alumina, and
rhenium oxide on alumina.

Presently preferred are those disproportionation catalysts which have been well characterized and are readily available, such as for example, tungsten oxide on silica support and molybdenum oxide on alumina support.

When preparing a mixed bed of double bond isomerization catalyst component and disproportionation catalyst component, particles of the two catalyst components having about the same particle size can be blended. Alternatively, both the double bond isomerization catalyst component and the disproportionation catalyst component can be intimately blended such as by grinding into a powder, the powder then being formed into other shapes such as pellets, tablets, agglomerates, extrudates, and the like, such that each particle in the catalytic zone comprises an intimate blend of the two catalyst components. As yet another alternative, a bed of double bond isomerization catalyst can precede the bed of disproportionation catalyst, such that the feed olefin contacts the double bond isomerization catalyst before coming into contact with the disproportionation catalyst component. Those of skill in the art recognize that other appropriate techniques for obtaining a composite of the two catalyst components can also be used.

The proportion of double bond isomerization component to the disproportionation catalyst component in the composite catalyst system can vary widely. At least about 0.1 part by weight of the double bond isomerization catalyst component should be present for each part by weight of the disproportionation catalyst component. There is no theoretical upper limit for the amount of the double bond isomerization catalyst component which can be present. Preferred ratios, for ease of catalyst blending, are about 0.5 up to about 20 parts by weight of the double bond isomerization catalyst component per part by weight of the disproportionation catalyst component. Ratios of about 2 up to about 10 parts by weight of the double bond isomerization catalyst component per part by weight of the disproportionation catalyst component are especially preferred because excellent catalyst performance is obtained when employing such ratios.

The composite catalyst systems prepared in accordance with the present invention are useful, for example, for the conversion of olefins via the olefin disproportionation or olefin metathesis reaction.

The disproportionation process of the present invention comprises contacting at least one olefin selected from the group consisting of acyclic mono- and polyenes having at least three up to 30 carbon atoms per molecule and cycloalkyl and aryl derivatives thereof; cyclic mono- and polyenes having at least four up to 30 carbon atoms per molecule and alkyl and aryl derivatives thereof; mixtures of two or more of the above olefins; and mixtures of ethylene with one or more of the above olefins capable of undergoing disproportionation with catalysts prepared according to the invention. Where mixtures of the above olefins with ethylene are subjected to disproportionation reaction conditions, it is desirable that the molar ratio of ethylene to olefin be at least 2. Preferably, ethylene;olefin ratios of about 4:1 or higher will be employed for good results.

Some specific examples of olefins suitable for the disproportionation reaction in accordance with this invention include propylene, 1-butene, 2-butene, 1-pentene, 2-pentene, 2,4,4-trimethyl-2-pentene and 2,4,4-trimethyl-1-pentene (diisobutylene isomers), 1-hexene, 1,4-hexadiene, 2-heptene, 1-octene, 2,5-octadiene, 2-nonene, 1-dodecene, 2-tetradecene, 1-hexadecene, 1-phenyl-2-butene, 4-octene, 3-eicosene, 3-hexene, vinylcyclohexane, 1,4-pentadiene, 1,4,7-dodecatriene, 2-methyl-4-octene, 4-vinylcyclohexene, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures of two or more thereof.

Some specific examples of cyclic olefins suitable for the reactions of this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclodecatriene, 1,4,7,10-cyclododecatetraene,, 6-methyl-6-ethyl-1,4-cyclooctadiene and the like, and mixtures of two or more thereof.

The reaction temperature can vary depending upon the catalyst(s) and feed(s) employed and upon the desired reaction products. Typically the disproportionation reaction is carried out at a temperature in the range of about 0° to about 600° C.; preferably for good conversion in relatively short reaction times, temperatures of from about 20° to about 500° C. are employed.

The disproportionation reaction can be carried out by contacting the olefins to be disproportionated with the catalyst in the liquid phase or the gas phase depending on the structure and molecular weight of the olefin. Pressure during the disproportionation reaction can vary between wide limits. For example, pressures between 0.1 and 500 atmospheres are suitable, although preferred pressures are between about 1 and 40 atmospheres because good conversions are obtained with readily available equipment.

If the reaction is carried out in the liquid phase, solvents or diluents for the reactants can be used. Aliphatic saturated hydrocarbons e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, and/or substantially inert gases, e.g. nitrogen, argon, can be present. Preferably, for high product yield, the disproportionation reaction is effected in the absence of significant amounts of deactivating materials such as water and oxygen.

The contact time needed to obtain a reasonable yield of disproportionation products depends upon several factors such as the activity of the catalyst, reaction temperature and pressure, as well as the structure of the olefinically unsaturated compound(s) to be disproportionated. The length of time during which the olefinic unsaturated compounds to be disproportionated are contacted with the catalyst can conveniently vary between 0.1 seconds and 24 hours although longer and shorter contact times can be used. Preferably, for efficient use of reactor equipment, times of about 1 second to about 1 hour are used.

The process of the invention can be effected batchwise or continuously with fixed catalyst beds, slurried catalyst, fluidized beds, or by using any other conventional contacting techniques.

The olefinic products of the invention have established utility including use as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form polyamides which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by reference to the following examples.

EXAMPLE I

Catalyst Preparation

The impregnated, alumina-supported isomerization catalysts used in the following examples were prepared by grinding the support to within the range of −20 to +40 mesh. A quantity (usually ~25 g) of ground support was then mixed with a comparable quantity (usually ~25 mL) of aqueous solution containing the desired amount of treating components. After the support had soaked in the aqueous solution for about 30 minutes, the water was removed by rotary evaporation of the slurry, and the resulting dried material subjected to calcination in a gentle air flow at about 350° C. for 2–3 hours. The metals employed and loading levels for catalysts prepared according to this procedure are summarized in Table II.

TABLE II*

| Catalyst | Metal, Loading Level (wt. %) | | |
|---|---|---|---|
| | Alkaline Earth | Alkali Metal | Other |
| A(control) | Ca,12.7 | Na, 0.5 | None |
| B(invention)** | Mg, 1.9 | None | None |
| C(invention)** | Mg, 3.8 | None | None |
| C'(invention) | Mg, 3.8 | None | None |
| C"(invention) | Mg, 3.8 | Na, 0.6 | None |
| D(invention)** | Mg, 3.8 | Na, 1.1 | None |
| E(invention)** | Mg, 3.8 | Na, 2.2 | None |
| F(invention) | Mg, 4.2 | Na, 0.5 | None |
| G(invention)** | Mg, 5.7 | None | None |
| H(invention) | Mg, 7.1 | Na, 0.5 | None |
| I(control)*** | Mg, 7.1 | Na, 0.5 | None |
| J(invention) | Mg, 7.1 | Na, 1 | None |
| K(invention) | Mg, 7.1 | Li, 0.34 | None |
| L(invention) | Mg, 7.1 | Li, 0.34 | None |

TABLE II*-continued

| | Metal, Loading Level (wt. %) | | |
|---|---|---|---|
| Catalyst | Alkaline Earth | Alkali Metal | Other |
| M(invention) | Mg, 7.1 | K, 0.8 | None |
| N(invention) | Mg, 8.6 | Na, 0.5 | None |
| O(invention) | Mg, 11.4 | Na, 0.5 | None |
| P(invention) | Mg, 11.4 | Na, 1 | None |
| Q(invention) | Mg, 13.3 | None | None |
| R(invention) | Mg, 13.3 | Na, 0.5 | None |
| S(invention)** | Mg, 3.8 | None | Zr, 1.4 |

*All catalysts were prepared using a support having a surface area of 220 $m^2/g$ and a pore volume of 0.95 $cm^3/g$, unless otherwise noted.
**Catalysts so designated were prepared with support having a surface area of 260 $m^2/g$ and a pore volume of 0.47 $cm^3/g$.
***Catalyst I was made with support having a surface area of 250 $m^2/g$ and a pore volume of 0.4 $cm^3/g$.

Disproportionation catalysts were prepared by spraying an aqueous solution of ammonium metatungstate on to silica support which was contained in a beaker fastened to a rotating table. The solution was added at a rate that permitted good absorption of the solution by the silica support. The amount of tungsten employed was sufficient to produce a catalyst having about 7.2 weight % $WO_3$ on $SiO_2$. The catalyst was dried in a moving stream of dry nitrogen, then heated at 100° C. for 0.5 hour and finally at 250° C. for 2 hours. Normally, this first catalyst component (1.5 grams) was mixed with the isomerization catalyst component, (3.8 g) and about 1.2 g of α-alumina as an inert diluent before activation. The mixture was then heated in the presence of air at 538° C. for 3–8 hours followed by heating at the same temperature in the presence of carbon monoxide for 10–30 minutes, and finally cooled to reaction temperature ready for the introduction of reactant feed.

EXAMPLE II

Olefin Isomerization-1-Butene

Runs were made with several different catalysts to isomerize Phillips Pure Grade butene-1. About 5 g of catalyst (−20+40 mesh) was placed in a ½" i.d. stainless steel reactor and the feed passed downflow at a feedrate of about 0.60 g/min. (or a WHSV of about 7) and a pressure of about 400 psig. Reaction temperature, actual catalyst used to charge the reactor and product analyses are presented in Table III. Products were analyzed by gas liquid chromatography (GLC).

TABLE III

| Run | | | Product Analysis, wt. %* | |
|---|---|---|---|---|
| # | Catalyst | Reaction Temp., °C. | 1-$C_4$ | 2-$C_4$ |
| 1 | MgO | 150 | 86 | 14 |
| 2 | MgO | 200 | 75 | 25 |
| 3 | MgO | 250 | 26 | 71 |
| 4 | MgO | 275 | 21 | 79 |
| 5 | A | 150 | No reaction | |
| 6 | F | 275 | 24 | 76 |
| 7 | H | 150 | 70 | 30 |
| 8 | I | 150 | No reaction | |
| 9 | H | 275 | 18 | 82 |
| 10 | K | 150 | 98 | 2 |
| 11 | N | 200 | 45 | 55 |
| 12 | O | 200 | 27 | 73 |
| 13 | P | 150 | 25 | 75 |
| 14 | Q | 150 | 39 | 61 |
| 15 | R | 170 | 20 | 80 |
| 16 | R | 200 | 17 | 83 |

*1-$C_4$ is 1-butene
2-$C_4$ is 2-butene

The results summarized in Table III indicate that magnesium on high surface area, high pore volume alumina is an active isomerization catalyst (see run 14 where high conversion is obtained at temperatures as low as 150° C.). At higher reaction temperatures and with optimal metal loading, nearly thermodynamic isomer ratios (1-butene/2-butene) are achieved (see run 9, for example).

EXAMPLE III

Olefin Isomerization -- 2-Butene

The procedure described in Example II was repeated, employing 2-butene as the olefin feed instead of 1-butene. Results are summarized in Table IV.

TABLE IV

| Run | | | Product Analysis, wt. %* | |
|---|---|---|---|---|
| # | Catalyst | Reaction Temp., °C. | 1-$C_4$ | 2-$C_4$ |
| 17 | MgO | 300 | 3 | 97 |
| 18 | J | 300 | 18 | 81 |
| 19 | R | 300 | 20 | 80 |
| 20 | R | 350 | 22 | 78 |

*1-$C_4$ is 1-butene
2-$C_4$ is 2-butene

These results demonstrate that invention isomerization catalyst is effective for conversion of 2-butene to a thermodynamic mixture of 1- and 2-butene.

EXAMPLE IV

Disproportionation of Ethylene plus Diisobutylene

All runs were made by passing ethylene and a mixture of diisobutylene isomers (2,4,4-trimethyl-1-pentene and 2,4,4-trimethyl-2-pentene) downflow through a vertical pipe reactor (½ inch diameter and 20 inches in length) positioned in a temperature-controlled electric furnace. A thermocouple was positioned in the catalyst bed to monitor reaction temperature.

About 5 inches depth of alpha-alumina particles were placed at the bottom of the pipe reactor supported with a layer of glass wool. The bed of alpha-alumina particles supported an admixture of 4.3 grams (g) $WO_3/SiO_2$ and 10.7 g of isomerization catalyst. This was topped with another layer of glass wool and the remaining reactor space filled with alpha-alumina. The catalyst was activated by heating at 538° C. in flowing air for 8 hours followed by a 30 minute treatment with flowing carbon monoxide at 538° C.

Ethylene used in the reaction was passed through a 13X mol sieve drier and diisobutylene employed was passed over a magnesium oxide guard bed. Feed was introduced into the reactor maintained at about 373° C. and 400 psig pressure. An ethylene:diisobutylene molar ratio of about 2:1 was introduced at a diisobutylene feed rate of about 30 weight hourly space velocity (WHSV). Product samples were collected in a high pressure syringe and were analyzed in a Hewlett Packard Model 5840 gas chromatograph using a ⅛"×20" column packed with 10% OV101 (dimethylsilicone available from Supelco, Inc., Bellefonte, Pa.) on Chromosorb P (red diatomaceous earth available from Applied Science, Deerfield, Illinois). Bomb samples of reaction off-gases were also collected and analyzed by GLC for ethylene and hydrogen. Reaction results are summarized in Table V.

TABLE V

| | Isomerization | | Gas Analysis, %* | |
|---|---|---|---|---|
| Run No. | Catalyst | Neohexene Yield | $C_2$ | $H_2$ |
| 21 | MgO | 53 | 70.5 | 0.75 |
| 22 | B | 56 | ND | ND |

TABLE V-continued

| | Isomerization | | Gas Analysis, %* | |
|---|---|---|---|---|
| Run No. | Catalyst | Neohexene Yield | $C_2$ | $H_2$ |
| 23 | C | 63 | 69.8 | 0.61 |
| 24 | C' | 62 | ND | ND |
| 25 | C'' | 76 | ND | ND |
| 26 | D | 64 | 73.3 | 0.67 |
| 27 | E | 56 | ND | ND |
| 28 | G | 57 | ND | ND |
| 29 | S | 61 | 72.6 | 0.44 |

*ND = not determined

The data in Table V show that mixtures of invention isomerization catalyst and disproportionation catalyst give enhanced product yields relative to prior art disproportionation isomerization catalyst systems (exemplified by Run 21 of Table V). In addition, the zirconium containing catalyst (catalyst S) significantly suppresses the amount of hydrogen by-product produced in the course of the desired conversion.

EXAMPLE V

Disproportionation of Ethylene plus 2-Butene

All runs were made by passing ethylene and a mixture of cis-and trans-2-butene downflow through a vertical pipe reactor (½ inch diameter and 20 inches in length) positioned in a temperature-controlled electric furnace. A thermocouple was positioned in the catalyst bed to monitor reaction temperature.

About 6 inches depth of quartz chips (−9+12 mesh) were placed at the bottom of the pipe reactor supported by a layer of quartz wool. Another layer of quartz wool was placed on top of the quartz chips as support for a combined catalyst bed comprising about 1.5 g of silica supported $WO_3$ catalyst mixed with about 3.8 g of isomerization catalyst as the second catalyst component. This was topped with another layer of quartz wool and the remainder of the reactor filled with quartz chips. The combined catalyst was activated by heating at 538° C. in flowing air for three hours, followed by about 15-minute treatment with flowing carbon monoxide at the same temperature and finally the catalyst was cooled under flowing nitrogen to reaction temperature.

Ethylene used in the reaction was passed through a 13X mol sieve drier and butene feedstock was percolated through 13X mol sieve, then alumina and finally magnesium oxide prior to use. Feed introduced into the reactor was maintained at about 400 psig pressure and between about 343° and 371° C. (650°-700° F.). Ethylene:butene molar ratios of about 3/1 to about 8/1 were investigated with a total feed introduction rate of about 30 weight hourly space velocity (WHSV).

The hot reactor effluent was vented to a hood; periodically the total effluent was sampled for analysis after 5 hours on stream using a modified, heated Series A-2 Sample-Lok syringe (Dynatech Precision Sampling Corporation). Analyses were carried out on a ⅛"×20'OV-101 column at an initial temperature of 50° C. programmed up to 200° C. Reaction results are summarized in Table VI. Values for conversion of 2-butene (Conv) presented in Table VI are calculated as weight percent; selectivity to propylene was essentially quantitative in all cases.

TABLE VI

| Run No. | Isomerization Catalyst | Reaction Temp, °C. | Conv |
|---|---|---|---|
| 30 | None | 330 | 31 |
| 31 | MgO | 330 | 67 |
| 32 | H | 300 | 70 |
| 33 | H | 330 | 75 |
| 34 | J | 240 | 73 |
| 35 | J | 270 | 78 |
| 36 | J | 270 | 67 |
| 37 | J | 270 | 75 |
| 38 | J | 300 | 77 |
| 39 | L | 270 | 74 |
| 40 | M | 270 | 59 |
| 41 | O | 270 | 62 |
| 42 | R | 270 | 55 |

Feed conversion is improved by the use of invention isomerization catalyst compared to magnesium oxide in nearly all cases summarized in Table VI. Note that runs 40–42 where feed conversion is lower than in control run 31, the reaction temperature is 60° lower than in the control run. Thus, the conversion values for runs 40–42 are still quite good when the temperature of reaction is considered.

The examples have been provided merely to illustrate the practice of my invention and should not be read so as to limit the scope of my invention or the appended claims in any way. Reasonable variations and modifications, not departing from the essence and spirit of my invention, are contemplated to be within the scope of patent protection desired and sought.

I claim:

1. In a disproportionation process wherein at least one olefin is contacted with a disproportionation catalyst under disproportionation conditions, the improvement comprises associating with said disproportionation catalyst an isomerization catalyst prepared by:

(a) impregnating an alumina support having a surface area of at least 200 $m^2/g$ and a pore volume of at least 0.45 $cm^3/g$ with:

1 up to 20 wt. % of at least one magnesium compound convertible to the oxide, based on the weight of support and calculated as the metal;

0 up to 5 wt. % of at least one alkali metal compound convertible to the oxide, based on the weight of support and calculated as the metal; and 0 up to 5 wt. % of at least one zirconium compound convertible to the oxide, based on the weight of support and calculated as the metal; and thereafter (b) heating the alumina support impregnated in accordance with step (a) in an oxygen-containing atmosphere under conditions suitable to convert at least a portion of said magnesium, alkali metal, and zirconium compounds to the oxide form.

2. A process in accordance with claim 1 wherein said disproportionation catalyst is selected from the group consisting of:

tungsten oxide on silica,
molybdenum oxide on alumina,
molybdenum oxide on silica,
cobalt molybdate on alumina, and
rhenium oxide on alumina.

3. A process in accordance with claim 1 wherein said disproportionation catalyst is tungsten oxide on silica.

4. A process in accordance with claim 1 wherein said magnesium compound is present in an amount within the range of 6–9 wt. %, said alkali metal compound is present in an amount within the range of 0.4–2.5 wt. %, and said zirconium compound is present in an amount within the range of 0.5–2 wt. %.

5. A process in accordance with claim 1 wherein said isomerization catalyst is present in an amount within the range of 0.5 to 20 parts by weight per part by weight of said disproportionation catalyst.

6. A process in accordance with claim 1 wherein said olefin is selected from the group comprising acyclic mono-and polyenes having at least three up to 30 carbon atoms per molecule and cycloalkyl and aryl derivatives thereof; cyclic mono and polyenes having at least 4 up to 30 carbon atoms per molecule and alkyl and aryl derivatives thereof; mixtures thereof; and mixtures of ethylene with one or more of the above olefins.

7. A process in accordance with claim 3 wherein said magnesium compound is present in an amount within the range of 6–9 wt. %, said alkali metal compound is present in an amount within the range of 0.6–2.5 wt. %, and said zirconium compound is present in an amount within the range of 0.5–2 wt. %.

* * * * *